US00PP36221P2

(12) United States Plant Patent
Hansoti

(10) Patent No.: US PP36,221 P2
(45) Date of Patent: Oct. 22, 2024

(54) ***SANSEVIERIA* PLANT NAMED 'HANSOTI41'**

(50) Latin Name: *Sansevieria trifasciata*
Varietal Denomination: HANSOTI41

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 18/426,474

(22) Filed: Jan. 30, 2024

(51) Int. Cl.
*A01H 5/12* (2018.01)
*A01H 6/12* (2018.01)

(52) U.S. Cl.
USPC ..... Plt./382
CPC ..... *A01H 6/12* (2018.05)

(58) Field of Classification Search
USPC ..... Plt./382
CPC ..... A01H 5/12
See application file for complete search history.

*Primary Examiner* — Kent L Bell

(57) ABSTRACT

A new and distinct cultivar of *Sansevieria* plant named 'HANSOTI41' is disclosed, characterized by unusual twisted, curled, compact foliage arranged in flattened, spiral rosettes. The new cultivar is a compact Birds Nest type *Sansevieria* forming small plants, reaching only about 12 cm in height at maturity. Plants require little water, having a moderate tolerance for drought, and are also tolerant of very wet conditions. Foliage is green and yellow-green banded with a dark-green margin. The new variety is a *Sansevieria*, typically produced as an indoor ornamental plant.

7 Drawing Sheets

Latin name of the genus and species: *Sansevieria trifasciata.*

Variety denomination: 'HANSOTI41'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI41'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI41' was discovered and selected by the inventor, Ashish Hansoti, as a single aberrant side shoot within a planting of *Sansevieria trifasciata* 'Hahnii Gold', a non-patented 'Hahnii' or 'Birds Nest' type of *Sansevieria* grown at a nursery in Village Vangani, District Thane, Maharashtra State in Western India. 'HANSOTI41' originated as a naturally-occurring mutation of the *Sansevieria trifasciata* variety 'Hahnii Gold', unpatented, in early 2018.

Asexual reproduction of the new *Sansevieria* cultivar by vegetative cuttings was first performed in March 2019 at a commercial nursery in Village Vangani, District Thane, Maharashtra State in Western India. This first and subsequent propagation have shown that the distinctive combination of characteristics of the new cultivar are reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'HANSOTI41', which in combination distinguish this *Sansevieria* as a new and distinct cultivar:

1. Twisted, curved leaves forming a relatively flat, somewhat open spiral-form rosette that stays vertically compact and gives a vertically compressed appearance as opposed to most other *Sansevieria trifasciata* 'Hahnii' cultivars where the leaves are more or less straight and more vertically oriented. The spiral rosette often is somewhat asymmetrical when seen from top. Total mature-plant width in a 12 cm pot is 15 to 17 cm and height above the pot is only 6 to 8 cm.
2. Leaf coloration and variegation pattern is also quite unique and very different from its parent, *Sansevieria trifasciata* 'Hahnii Gold'. Overall colour impression is of an olive green *Sansevieria* with streaks of cream and greyish green.

'HANSOTI41' has foliage variegation that is unlike its parent or, indeed, any other Hahnii, know to the Inventor, type along with the very unusual vertically-flat spiral foliage arrangement, asymmetrical when seen from top, giving an overall extremely distinctive and unique appearance.

Leaf width is somewhat variable and the strongest, healthiest plants have the widest leaves (this is true across all *Sansevieria trifasciata* cultivars known to the inventor) though leaves in 'HANSOTI41' are relatively narrow. This variation means leaf width can be anything from 3 cm to 4 cm wide depending on season, growing conditions and plant vigour and plant age. Typically, the leaves are of medium width (5 cm average measured at the widest part of the mature leaf under good growing conditions) and 12-16 cm long, ensiform but not erect; rather, most unusually, they are held almost perfectly horizontally. Leaves have a firm, waxy texture. The blades are thick and fleshy.

The new variety 'HANSOTI41' is a variety of *Sansevieria* in the group denominated as "Birds Nest" or 'Hahnii' types based on its origin and overall plant form. The new variety presents an average of 12 leaves per plant when it reaches its saleable size (about 3 months from rooted Liner) but over time it can grow and accumulate many more leaves and increase in overall height.

The new variety is moderately drought tolerant and adapts well to conditions of bright light or heavy shade (exterior and interior). The intensity of leaf colour varies with exposure to light and the contrast is most intense under higher light conditions.

The leaves show a variegated colouration, with broad green borders having a central area of cream liberally interspersed with grey-green streaks. The typical *Sansevieria trifasciata* cross hatching along the width of the leaf is distinctly seen. The amount of cream colour is variable but generally it is overwhelmed by the darker green longitudinal bands. Younger leaves, side shoots and plants tend to show more creamy coloration. Older leaves are darker green.

Each leaf has a marginal deep green band similar to RHS Yellow-Green N189A and varies in width from just 3 mm to 15 mm. Within this dark olive-green border is creamy coloration close to Yellow 160A, overlaid to varying degrees (but covering most of the centre of each leaf) with streaks similar to Grey-Green 191C and occasional darker green streaks of Yellow-Green 189B.

The backside of the leaves is also distinctive—a relatively thin 1 mm to 10 mm wide border of dark olive green with a visually uniform creamy coloration between these dark borders with the grey-green pattern of the top of the leaf showing in the depths below this cream layer. The backside of the leaf also has the typical *Sansevieria trifasciata* transverse banding but this banding is light and indistinct—near RHS Yellow-Green154B interspersed with transverse bands similar to but somewhat lighter than Yellow 2D—observable only on close inspection.

Attached colour pictures are a better guide to the complex leaf arrangement and the overall colouration and variegation pattern rather than written descriptions and are the best reference to compare the new plant invention 'HANSOTI41' to older and newer *Sansevieria trifasciata* 'Hahnii' mutants. The primary distinctive characteristics of 'HANSOTI41' are the curved, twisted leaves forming a flat, vertically compact disc and the atypical variegation colour and pattern of these twisted leaves.

PARENTAL COMPARISON

Plants of the new *Sansevieria* 'HANSOTI41' are similar to plants of the parental cultivar, however, 'HANSOTI41' differs in the characteristics described in Table 1.

TABLE 1

Comparison of Parent Cultivar 'Hahnii Gold' and New variety 'Hansoti41'

| | Characteristic | Parent Cultivar 'Hahnii Gold' | New cv 'Hansoti41' |
|---|---|---|---|
| 1. | Leaf | 9 to 13 cm long, straight but held in a flat rosette so individual leaf is held somewhat at an angle. | 12 to 16 cm long, twisted and curved and held horizontally to form a vertically flat, spiral rosette |
| 2. | Number of leaves | 11 to 14 leaves | 11 to 14 leaves |
| 3. | Variegation Pattern | 1-3 mm dark green stripe followed by a 8-15 mm wide bright cream border band with grey green centres and with relatively mild *S. trifasciata* transverse banding. | Dark, olive-green bands on both sides with cream centres liberally streaked with grey green bands and darker green stripes. |
| 4. | Border variegation | 2 to 15 mm light green band | 5 to 15 mm wide dark green band |
| 5. | Central Variegation | Central wide band of greyish green streaked with creamish-green. Transverse banding indistinct but present. | 2 to 3 cm wide band of creamy yellow with streaks and bands of grey-green and stripes of dark green. *S. trifasciata* Transverse banding indistinct but seen. |

COMMERCIAL COMPARATOR

Plants of the new *Sansevieria* 'HANSOTI41' are similar to the commercial variety *Sansevieria* 'Hansoti21', U.S. Plant Pat. No. 33,168. Plants of the new *Sansevieria* 'HANSOTI41' differ from plants of the commercial cultivar 'Hansoti21' in the characteristics described in Table 2.

TABLE 2

Comparison of Closest Similar Cultivar 'Hansoti21' and New variety 'Hansoti41'

| | Characteristic | Similar Cultivar 'Hansoti21' | New cv 'Hansoti41' |
|---|---|---|---|
| 1. | Leaf | 8 to 13 cm long (Shorter) and 4-6 cm wide (Wider) | 12 to 16 cm long (Longer) and 3 to 4 cm wide (Narrower) |
| 2. | Number of leaves | 9 to 11 leaves (Fewer leaves) | 11 to 14 leaves (More leaves) |
| 3. | Variegation Pattern | Creamy yellow border band and green leaf centre prominently marked with typical *S. trifasciata* transvers banding. | Dark, olive-green border bands on both sides with cream centres liberally streaked with grey green bands and darker green stripes. |
| 4. | Border variegation | 3 to 12 mm creamy yellow band | 5 to 15 mm wide dark olive-green band |
| 5. | Central Variegation | The transverse light green banding typical of *S. trifasciata* seen | 2 to 3 cm wide band of creamy yellow obscured by streaks or bands of grey-green and stripes of dark green. Transverse banding faint but present. |

BRIEF DESCRIPTION OF THE PHOTOGRAPHS

The accompanying photographs illustrate the overall appearance of the new *Sansevieria* cultivar 'HANSOTI41' showing the colors as true as is reasonably possible with colored reproductions of this type. Colors in the photographs may differ slightly from the color value cited in the detailed botanical description which accurately describe the color of 'HANSOTI41'.

These pictures illustrate the plant form which is the unique characteristic of 'HANSOTI41' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

DETAILED BOTANICAL DESCRIPTION

Figure 1:
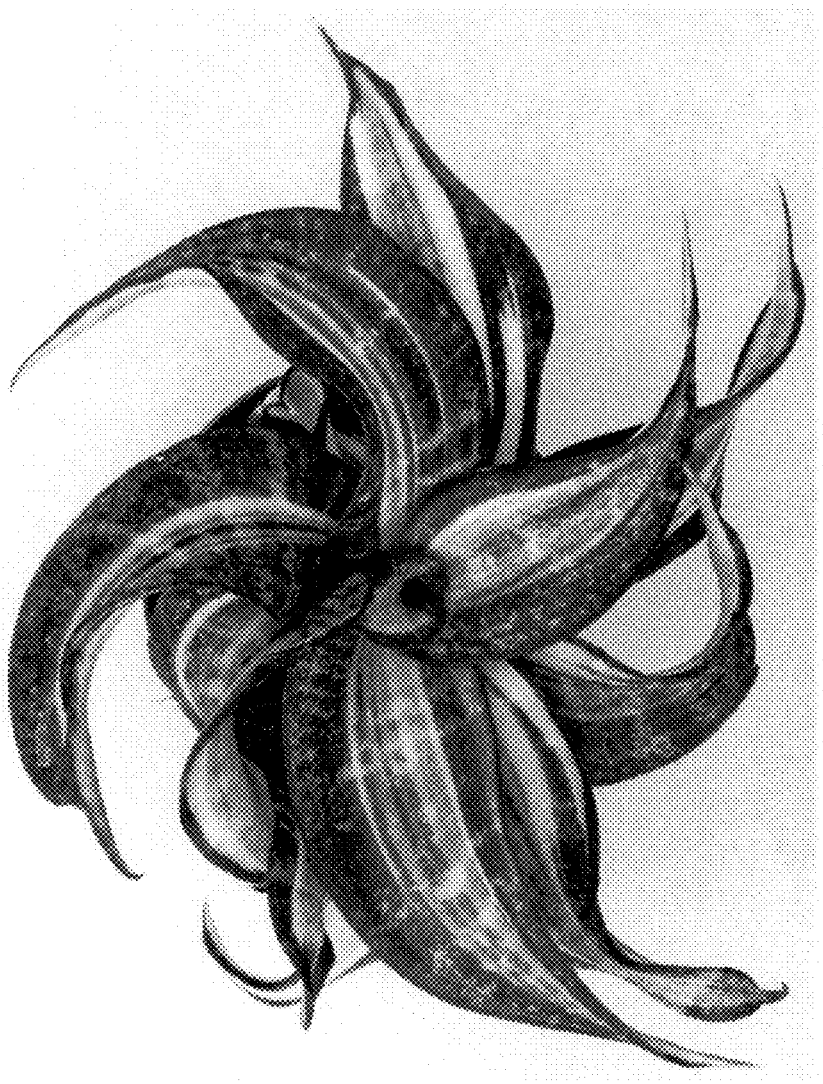
FIG. 1 shows a top view of a 12 to 14 week-old plant of *Sansevieria* 'HANSOTI41' in a 12 cm diameter pot.
Figure 2:
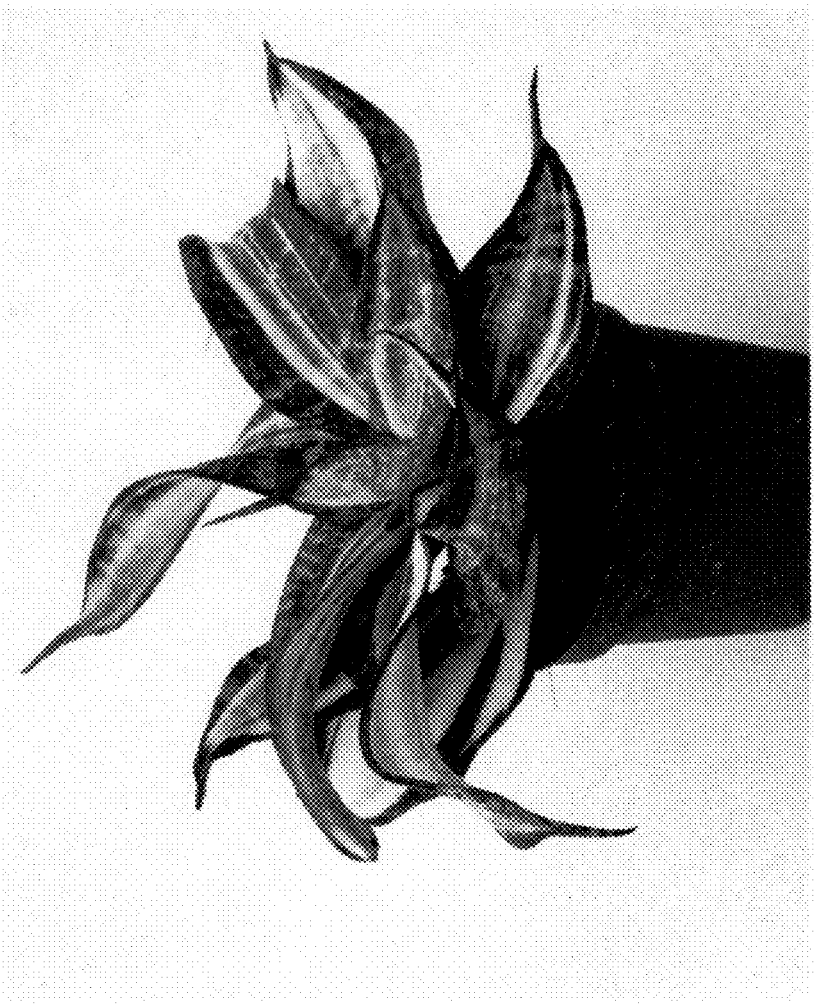
FIG. 2 shows a side view of a 12 to 14 week-old plant of *Sansevieria* 'HANSOTI41' in a 12 cm diameter pot.
Figure 3:
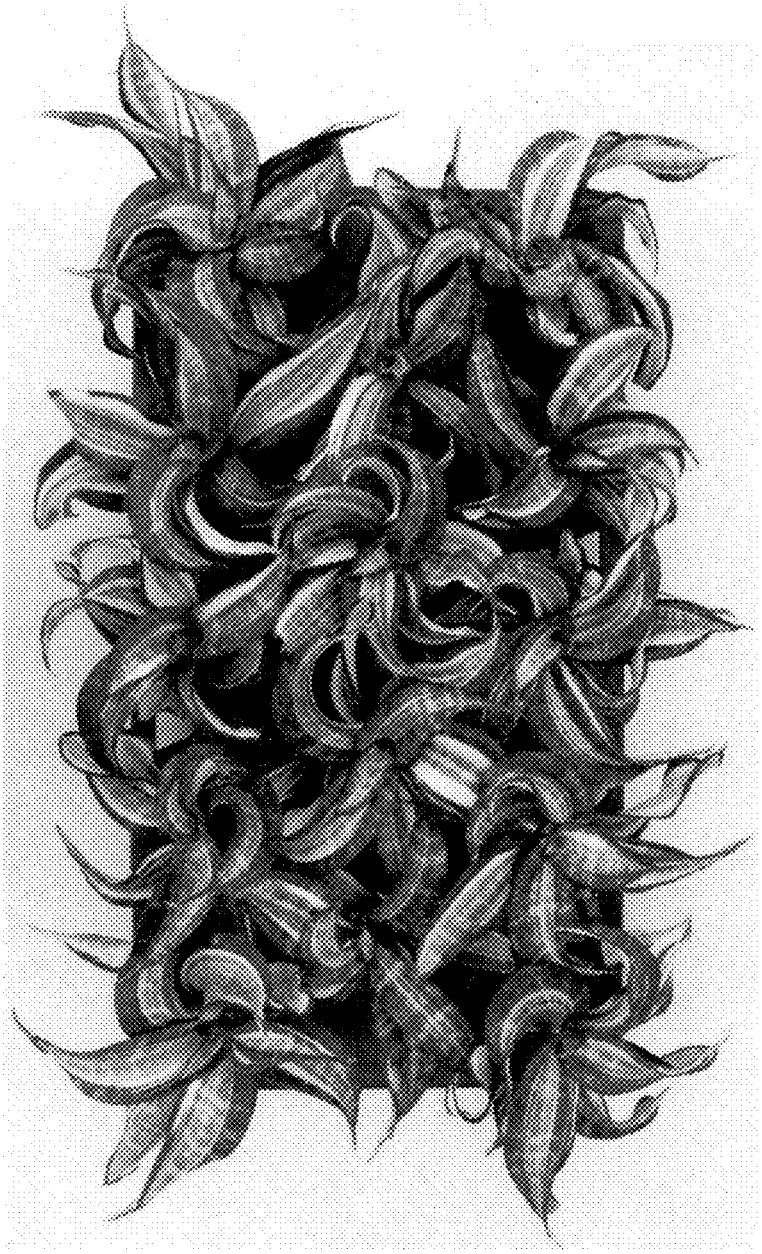
FIG. 3 shows a tray holding 14 'HANSOTI41' plants in 12 cm pots showing uniformity across multiple plants of this new cultivar.
Figure 4:
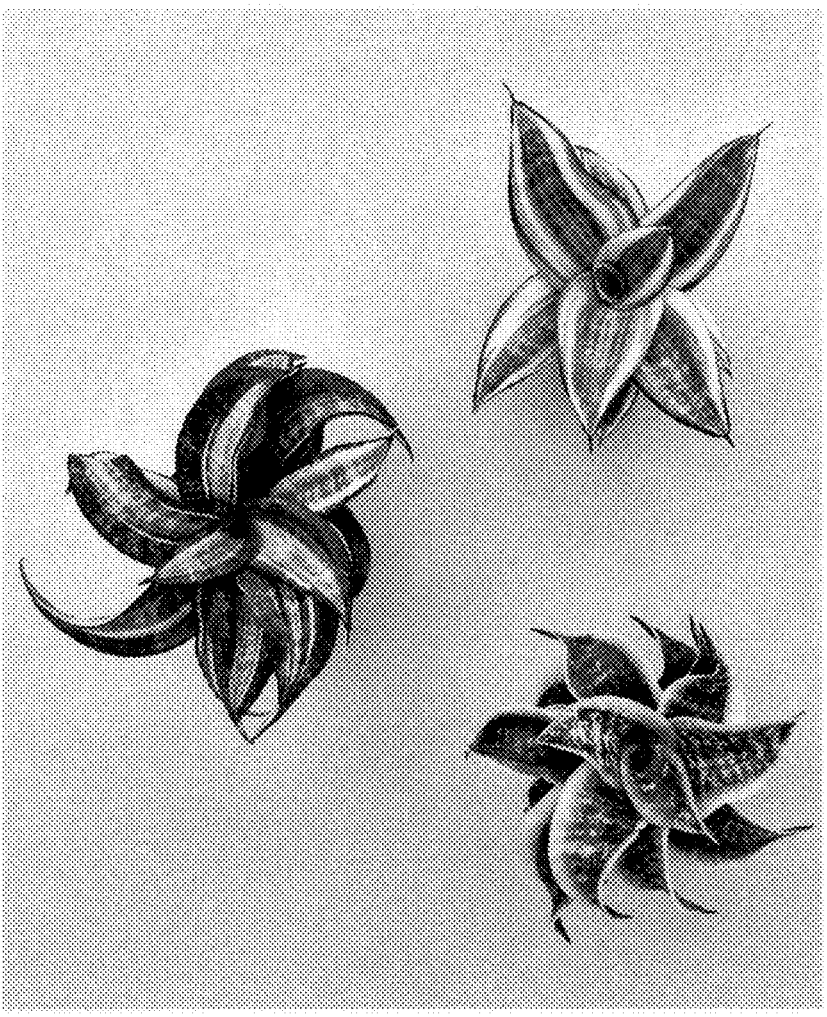
FIG. 4 shows 'HANSOTI41' beside the parent plant, *Sansevieria* 'Hahnii Gold', as well as the other comparable variety *Sansevieria* 'Hansoti21', alongside a plant of 'HANSOTI41' to compare the three. *Sansevieria trifasciata* 'Hahnii Gold'(Bottom right), *Sansevieria* 'Hansoti21'(Bottom left) compared with a more mature plant of *Sansevieria trifasciata* 'Hansoti41'(Top).
Figure 5:
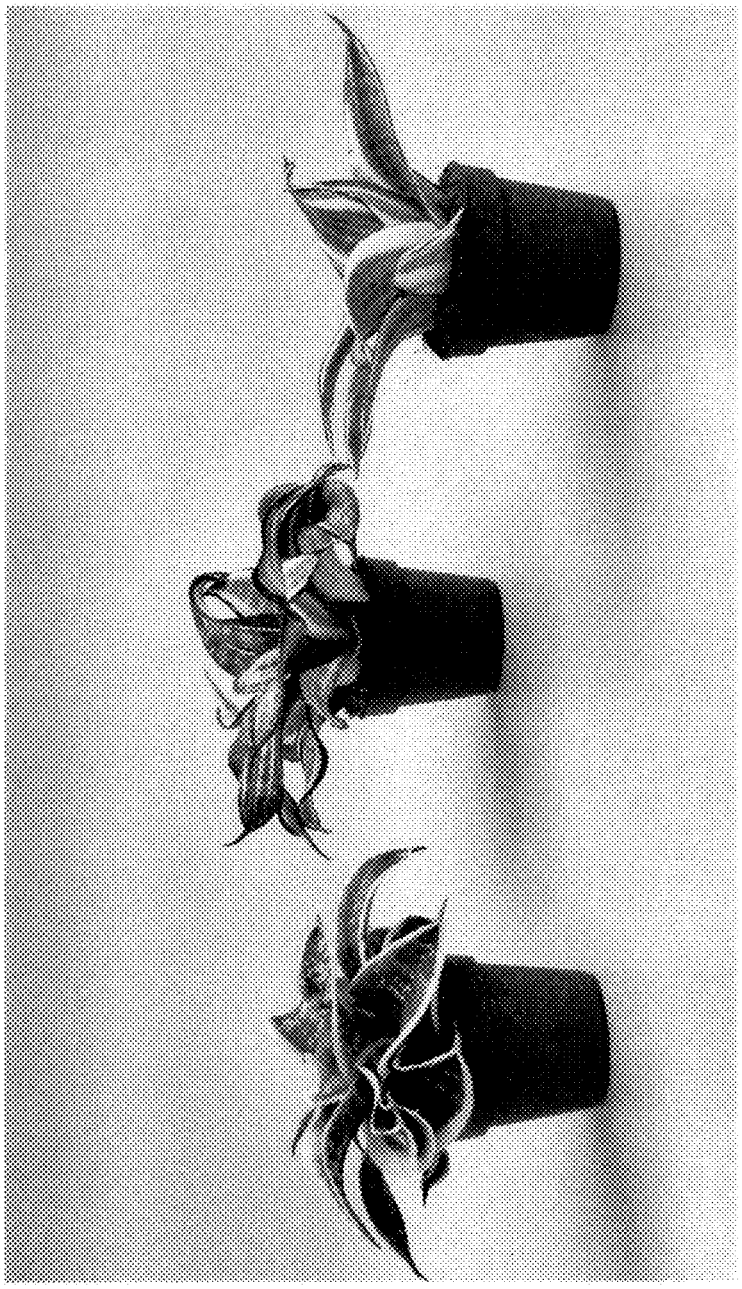
FIG. 5 shows the same plants from FIG. 4, from a side view. The novel shape and arrangement of leaves, variegation and coloration as entirely different from the parent is obvious.
Figure 6:
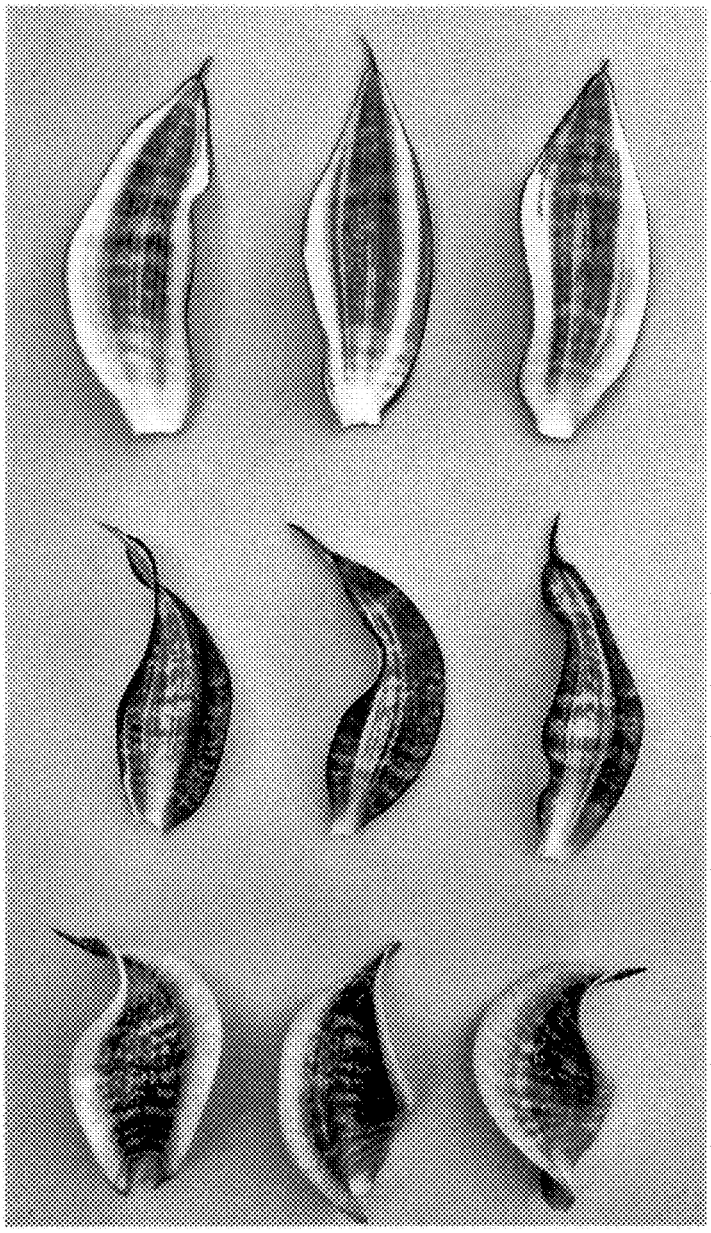
FIG. 6 shows a comparison of individual leaves(adaxial/top surface) of *Sansevieria* 'Hahnii Gold'(Top) as well as leaves of 'Hansoti21'(Bottom) with leaves of *Sansevieria* 'HANSOTI41'(Middle) to allow comparison between all three cultivars.
Figure 7:
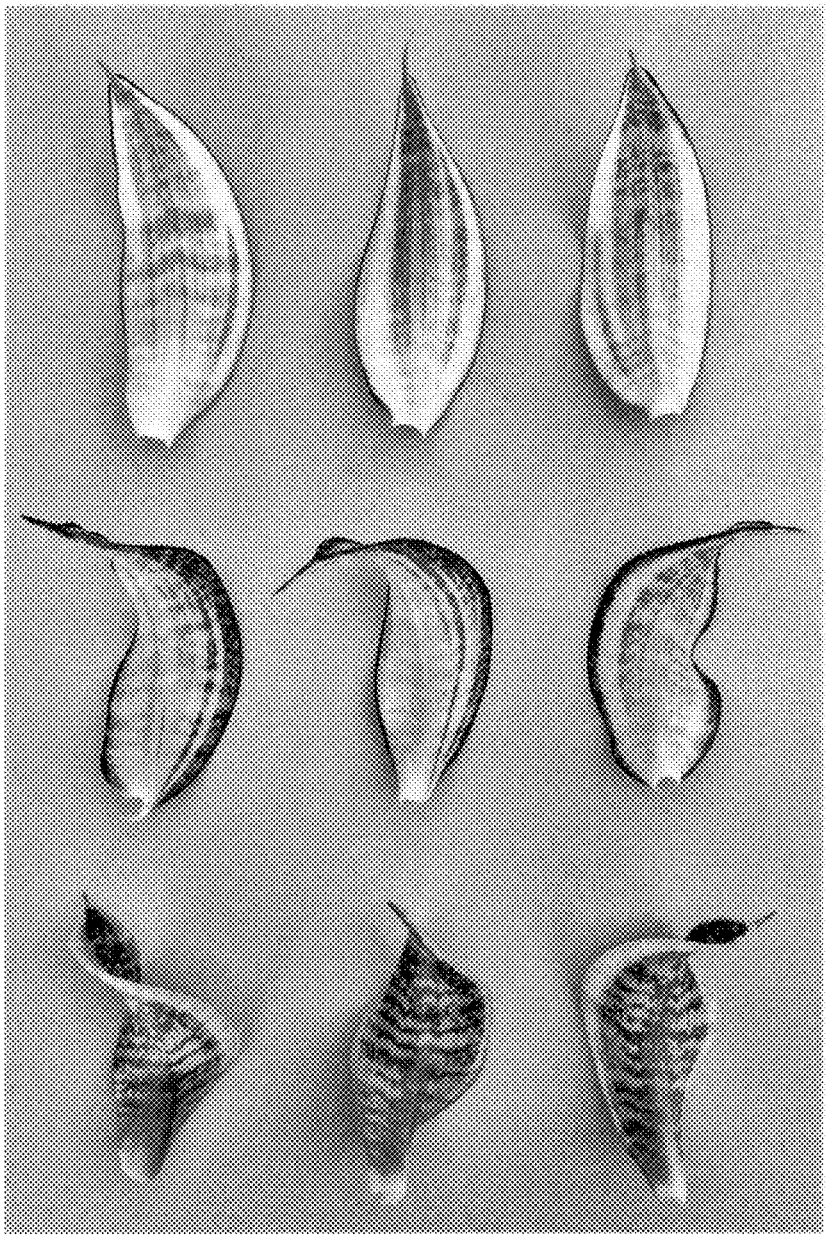
FIG. 7 shows a comparison of individual leaves (abaxial/bottom surface) of the three cultivars as above, again to show and compare the three cultivars variegation and coloration patterns. *Sansevieria* 'Hahnii Gold'(Top), 'Hansoti21'(Bottom) *Sansevieria* 'HANSOTI41'(Middle).

The new *Sansevieria* 'HANSOTI41' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI41' plants grown in an open poly house(high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertiliser of 13:11:11 Type 360-days release at 1 kilo/cubic meter of media, Constant Liquid Feed at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2009) except where general colors of ordinary significance are used.

The photographs and descriptions were taken during the monsoon season in Asle, District Satara, Maharashtra State, India when outdoor day temperature was 25° C. to 28° C. The age of the plants described is 3-4 months.

Botanical classification: *Sansevieria trifasciata* 'HANSOTI41'.

General information:

*Parentage.*—*Sansevieria trifasciata* 'Hahnii Gold' (unpatented).

*Optimal growth conditions.*—

*Light intensities.*—High adaptability to outdoor or indoor conditions.

*Temperature.*—Day: 25° C. to 35° C. Night: 15° C. to 25° C.

*Temperature tolerance.*—Tolerant to a low temperature of about 6° C. and a high temperature of 38° C. and above — very heat tolerant.

*Fertilization.*—Constant feed of 100 ppm N, 20 ppm P and 100 ppm K is used along with micronutrients with occasional leaching. Slow-release 13:11:11 added at 1 kg/cubic meter of growing media.

*Growth regulators.*—Not necessary for growth, however rooting hormone aids in rapid and prolific rooting of offsets.

Propagation:

*Typical.*—Vegetative, by side suckers which come true to type.

*Rooting habit and description.*—Rhizomes are elongated, fleshy, giving rise to offsets (side shoots). Offsets root easily with fibrous adventitious roots from cut end. Rooting hormone helps in faster and more prolific rooting. Colored cream to brown, not accurately measured with RHS chart.

*Time to initiate roots.*—15 to 20 days at 25° C. to 30° C.

*Time to produce a rooted liner.*—About 45 days at 25° C. to 30° C.

*Time to produce ready* 12 *cm potted plant from liner.*—About 3 months at 25° C.to 30° C.

Plant:

*General appearance and form.*—Monocot; leaf bases arranged in a rosette around growth point.

*Height.*—About 12 to 15 cm when grown in 12 cm pots.

*Spread.*—About 15 to 17 cm when grown when grown in a 12 cm size container.

*Growth rate and habit.*—Moderate growth rate, stays flat and compact.

*Shape.*—Rosette. Twisted, curved leaves form a vertically flattened plant rosette.

*Fragrance.*—None.

*Stem.*—Modified (Rhizomes which are fleshy with erect foliage, branching and giving offsets so forming clumps in time).

*Rosette height.*—About 6 to 8 cm height from top of pot when grown in 12 cm size container.

*Rosette diameter.*—About 15 cm to 17 cm.

*Texture.*—Smooth, waxy.

*Strength.*—Strong and durable.

*Internode length.*—About 1 mm.

Foliage:

*Quantity.*—About 11 to 14 in ready to sell plant. Number slowly increases with age.

*Arrangement and attachment.*—Single, alternate; leaf bases arranged stiffly in a twisting rosette around central growth point.

*Leaf length.*—About 12 to 16 cm, full-size leaf.

*Leaf width.*—About 3 to 4 cm, full-size leaf.

*Overall shape of leaf.*—Lanceolate.

*Apex shape.*—Acute, triangular and aristate, with soft tip.

*Base shape.*—Truncate, non-clasping.

*Margin.*—Sharp, smooth.

*Texture.*—Upper Surface: Smooth and waxy texture.

*Texture.*—Under Surface: Smooth and waxy texture.

*Pubescence.*—None.

*Color of mature leaf.*—Upper Surface: Dark green border near RHS Yellow-Green N189A with cream interior between these borders near Yellow 160A, liberally and largely covered with streaks of Yellow-Green 191C to 189B.

*Margins.*—Dark Olive green similar to RHS Yellow-Green N189A.

*Crossbanding.*—Seen on top surface, especially within the green borders; visible but indistinct on bottom surface of leaf.

*Color of mature leaf.*—Lower Surface: Mostly cream-yellow of RHS Yellow-Green 154B with very indistinct transverse banding similar to but somewhat lighter than Yellow 2D and with a thin dark green N189A border along the edges of the leaf.

*Venation.*—Pattern: Longitudinal/parallel leaf shape.

*Venation color.*—Indistinguishable from leaf blade.

*Leaf fragrance.*—None.

Other:

*Inflorescence description.*—Flowers not observed to date.

*Weather resistance.*—Moderately drought tolerant.

*Pest resistance.*—Reasonably resistant to pests, susceptible to root mealybugs (*Rhizoecus pritchardi*). Typical pests include *Pseudococcidae longispinus* and *Tetranychus urticae.*

*Disease resistance.*—Occasionally shows Anthracnose and leaf spots but largely disease free from clean mother stock.

*Fruit/seed production.*—No fruits/seeds detected to date.

What is claimed is:

1. A new and distinct cultivar of *Sansevieria* plant named 'HANSOTI41' as herein illustrated and described.

* * * * *